United States Patent [19]
Shichman

[11] Patent Number: 5,201,746
[45] Date of Patent: Apr. 13, 1993

[54] SURGICAL HEMOSTATIC CLIP

[75] Inventor: Daniel Shichman, Trumbull, Conn.

[73] Assignee: United States Surgical Corporation, Norwalk, Conn.

[21] Appl. No.: 777,083

[22] Filed: Oct. 16, 1991

[51] Int. Cl.⁵ .............................................. A61B 17/00
[52] U.S. Cl. ................... 606/151; 606/157; 606/158; 227/902
[58] Field of Search ............... 606/158, 157, 151, 143; 24/556, 546, 545; 227/902

[56] References Cited

U.S. PATENT DOCUMENTS

| | | | |
|---|---|---|---|
| 700,478 | 5/1902 | Carpenter | 24/545 |
| 3,006,344 | 10/1961 | Vogelfanger . | |
| 3,363,628 | 1/1968 | Wood . | |
| 3,867,944 | 2/1975 | Samuels . | |
| 4,188,953 | 2/1980 | Klieman et al. . | |
| 4,278,091 | 7/1981 | Borzone . | |
| 4,407,286 | 10/1983 | Noiles et al. . | |
| 4,412,539 | 11/1983 | Jarvik | 606/158 X |
| 4,449,530 | 5/1984 | Bendel et al. . | |
| 4,489,875 | 12/1984 | Crawford et al. . | |
| 4,519,392 | 5/1985 | Lingua . | |
| 4,531,522 | 7/1985 | Bedi et al. . | |
| 4,570,623 | 2/1986 | Ellison et al. . | |
| 4,624,254 | 11/1986 | McGarry et al. | 606/143 |
| 4,702,247 | 10/1987 | Blake, III et al. . | |
| 4,799,481 | 1/1989 | Transue et al. . | |
| 4,844,066 | 7/1989 | Stein . | |
| 4,971,198 | 11/1990 | Mericle | 606/158 |
| 4,976,722 | 12/1990 | Failla . | |
| 4,979,950 | 12/1990 | Transue et al. . | |

OTHER PUBLICATIONS

New LIGACLIP Extra Ligating Clips by Ethicon, Incorporated.
ENDO CLIP ® Booklet by United States Surgical Corporation.
STILLE Product Literature.

Primary Examiner—Stephen C. Pellegrino
Assistant Examiner—Jeffrey A. Schmidt
Attorney, Agent, or Firm—Thomas R. Bremer; Peter G. Dilworth; Rocco S. Barrese

[57] ABSTRACT

A hemostatic clip to be applied to body structures such as veins, arteries, or the like. The hemostatic clip includes a plurality of preferably semicircular indentations arranged in staggered row configuration on the tissue contacting surface of the legs of the clip.

19 Claims, 2 Drawing Sheets

SURGICAL HEMOSTATIC CLIP

BACKGROUND OF THE INVENTION

1. Field of the Invention

The present invention relates to a surgical clip, and more particularly to a hemostatic clip to be applied to blood vessels.

2. Background of the Art

Ligation or occlusion of veins, arteries or blood vessels has been a necessary part of surgical procedures for many years. Initially, surgeons used thread or suture material to tie a blood vessel prior to severing the vessel. This procedure required both skill and time on the part of the surgeon to properly close the vessel. In many instances, assistance of a nurse or attending surgeon was necessary and typically, a severed blood vessel would require closure on both sides of a severance site before actual cutting could take place. The advent of surgical clips and clip appliers has greatly enhanced this procedure.

Surgical clips are now commonly used and various types of surgical hemostatic clips are described in U.S. Pat. Nos. 4,976,722; 4,844,066; 4,702,247; 4,188,953; 3,867,944; and 3,363,628.

Many factors are critical to the design of a surgical clip. Among these, it is important that the clip not slip or become dislodged from a blood vessel after the blood vessel is severed. In that instance, blood will immediately begin flowing into the surgery site through the unclamped vessel requiring the operation be delayed while the critical vessel is located and reclamped. Depending on the type and location of the surgery, locating the vessel may be difficult and the time delay could cause medical complications to the patient.

Similarly, a clip must be designed to fully and completely close about a vein, artery or blood vessel and completely stop the flow of blood through these pathways. A clip which does not completely occlude the flow of blood is useless for its intended function. In addition, if the clip is of such a size or is designed in such a manner that during deformation about a vessel a portion of the vessel is allowed to extend beyond the tips of the clip legs, the clip will obviously not completely restrict the flow of blood and similar serious problems could arise. Consequently, besides insuring that the vessel is completely trapped within the clip, the clip must be designed such that when it is completely formed about a vessel the flow of blood through the vessel is completely precluded.

Generally, surgical clips are U-shaped or V-shaped members having two legs joined at an apex or crown portion and spaced apart at the opposite end. The inside or tissue-engaging surfaces of the clip legs may be treated in some manner, such as having spaced of grooves, in an attempt to improve the occluding functions of the clip and restrict movement of the clip after the clip has been deformed about a blood vessel. See, e.g., U.S. Pat. No. 4,799,481 to Transue et al.

Despite known clip designs, an improved clip is needed to provide optimum vessel occlusion and clip retention on tissue.

SUMMARY

A hemostatic clip for application to body tissue, such as blood vessels, is provided herein. The hemostatic clip includes first and second legs, each leg having a tissue contacting surface and at least two side surfaces intersecting said tissue contacting surface and defining a width of said leg therebetween. The tissue contacting surface has at least one indentation disposed thereon across less than the entire width of the tissue contacting surface and intersecting a side surface. Preferably, the indentations are semicircular and each leg includes a plurality of indentations arranged in staggered arrangement in first and second rows, the indentations intersecting with a respective one or the other of the side surfaces. The intersection of the indentation with the side surfaces defines an opening in the side surface to facilitate the flow of blood or other body fluids to the body tissue held by the clip. The hemostatic clip of the present invention provides excellent vessel occlusion and resists movement in directions both longitudinally along and transverse to the clipped blood vessel.

DETAILED DESCRIPTION OF PREFERRED EMBODIMENTS

The surgical clip of the present invention is a generally U-shaped or V-shaped member which is applied by an appropriate clip applying apparatus. The clip applying apparatus generally has means to position the clip around body tissue such as a blood vessel, and means to deform the clip, usually be bending the clip at its apex so that the legs of the clip close off the blood vessel. Two surgical fastener applying instruments suitable for use in applying the surgical clip of the present invention are disclosed and described in U.S. Pat. No. 4,509,518 to McGarry et al. and U.S. application Ser. No. 07/381,265 filed on Jul. 18, 1989, both of which are herein incorporated by reference.

Figure 1:
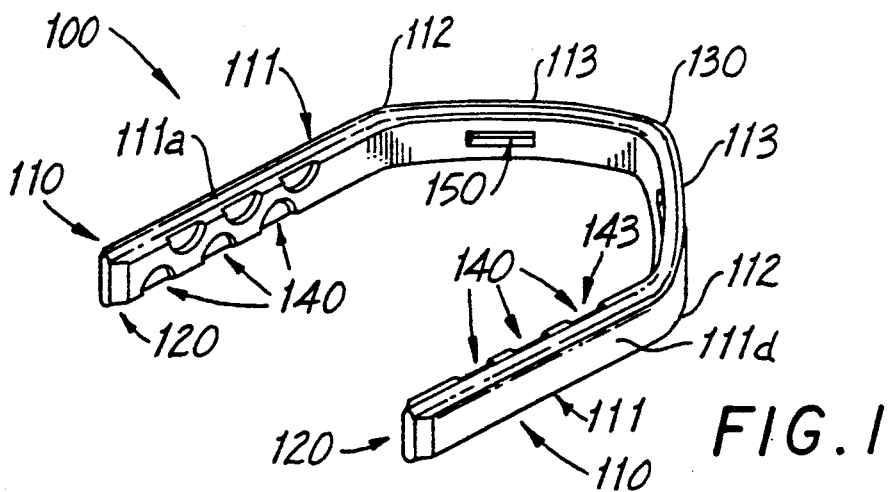
FIG. 1 is a perspective view of the surgical clip of the present invention.
Figure 2:
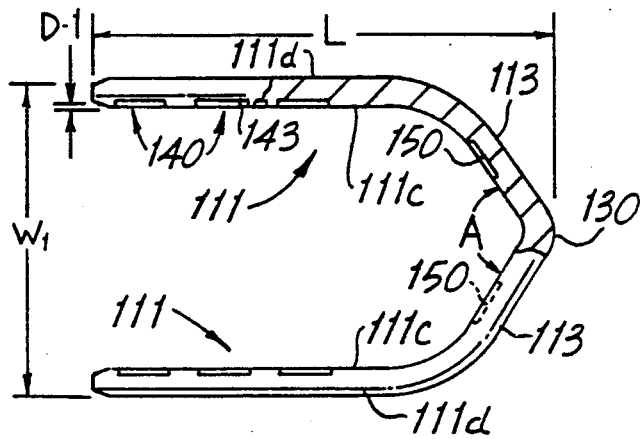
FIG. 2 is a plan view of the surgical clip.
Figure 5:
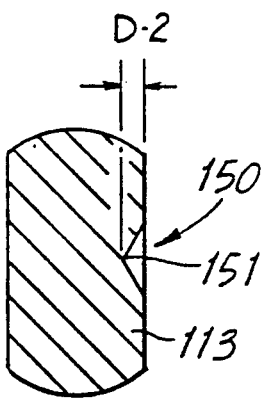
FIG. 5 is a sectional view illustrating a V-shaped notch in the clip.
Figure 3:
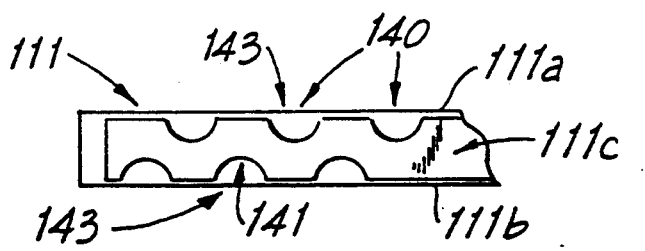
FIG. 3 illustrates the inner side of a leg of the surgical clip.
Figure 4:
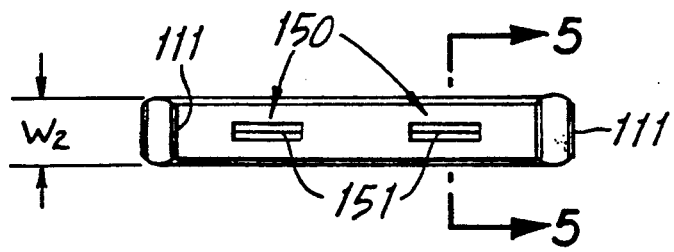
FIG. 4 is an end view of the surgical clip.

Referring to FIG. 1, the surgical clip 100 includes legs 110 having parallel distal end portions 111, curved portions 112, and proximal portions 113 of the legs which culminate in apex 130 and together form a generally V-shape or U-shaped bail end of the clip. The parallel end portions 111 of the legs include on their respective inner, tissue contacting surfaces 111c, a plurality of indentations 140 and bevelled ends 120. The end portions also include outer surfaces 111d, and upper and lower surfaces 111a and 111b, respectively. The side surfaces 111a and 111b define planes generally transverse to the planes of the inner and outer surfaces 111c and 111d. The proximal portions 113 each include on their inner surface an elongated notch 150 extending lengthwise along the portions 113. The notch 150 has a generally V-shaped cross section.

More particularly, referring to FIGS. 2, 3, 4, and 5, the surgical clip 100 includes two staggered rows of generally semicircular indentations 140 on the inner surfaces of each of the distal end portions 111 of the legs 110. There are three indentations 140 per row. The indentations 140 each comprise an arcuate wall 141 defining an open area 143 bounded by the intersection of the arcuate wall 141 with a respective one of the side surfaces 111a and 111b, the open areas 143 allowing fluid flow into body tissue contained in the indentations when the clip is applied to the organic body structure. The open areas 143 of one row of indentations on one leg 110 face in a direction opposite to the indentations 143 of the other, staggered row on the same leg. While a semicircular shape is preferred for the arcuate wall other arcuate and non-arcuate configurations are also usable. Notches 150 provide added tissue resistance. Apex 130 facilitates the crimping of clip 100 when the clip is applied to body tissue by a clip applicator.

The clip 100 may be of any dimension suitable for application to body tissue. In one preferred embodiment, the length L of the clip is about 0.3 inches, the width $W_1$ of the clip is from about 0.212 to about 0.216 inches, the width $W_2$ of the clip's legs is from about 0.034 to about 0.036 inches, the radius of the indentations is about 0.014 inches, the depth D-1 of the indentations 140 is from about 0.005 to about 0.007 inches, and the depth D-2 of the notch 150 is from about 0.002 to about 0.004 inches along the center line. The angle A formed by proximal portions 113 preferably can be from about 129° to about 131°. One skilled in the art will recognize that other dimensions can also be used.

The clip 100 can be fabricated from any surgically suitable material such as stainless steel, titanium, tantalum, or other metal alloys, as well as plastics including bioabsorbable polymers.

Figure 6:
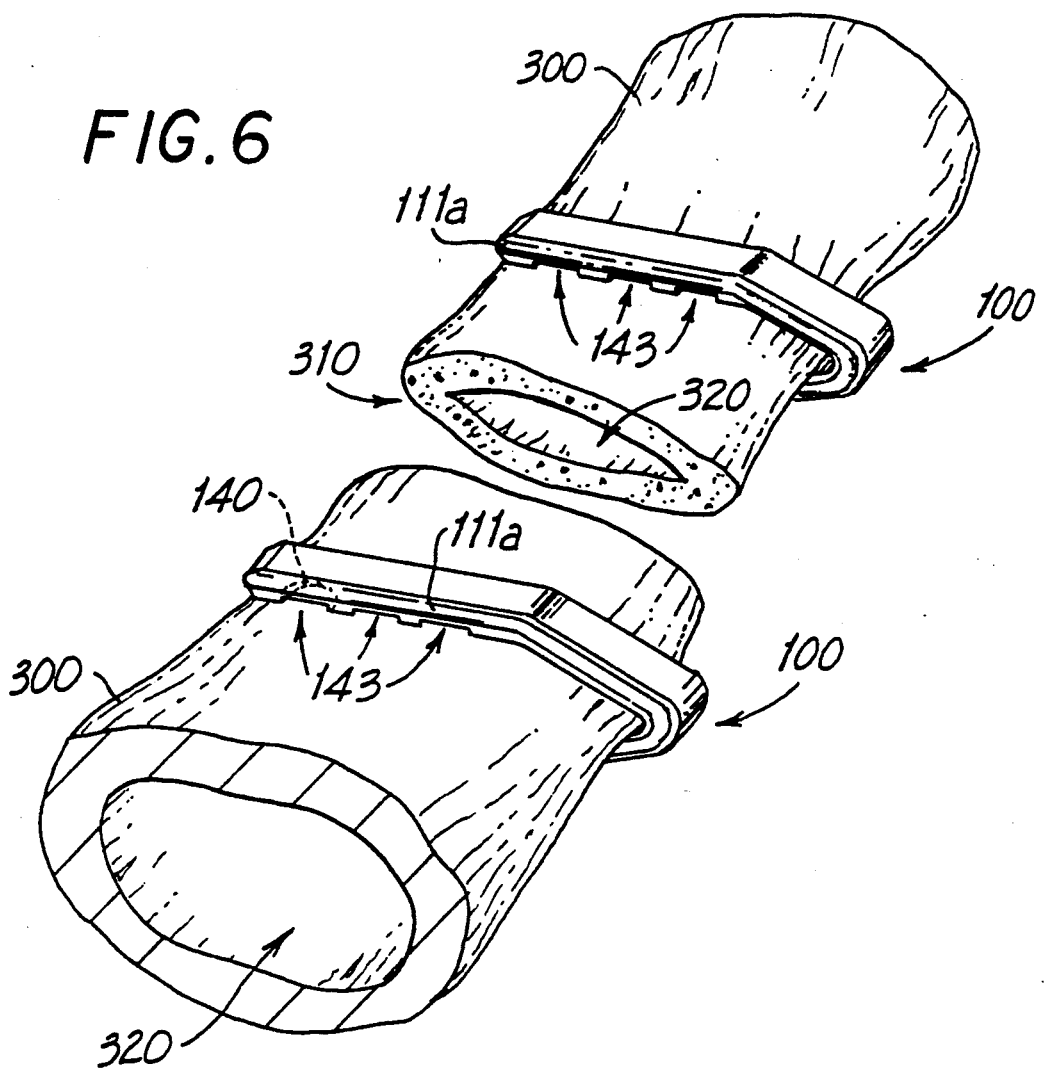
FIG. 6 is a perspective view illustrating the application of the clip of the present invention to a tubular organic structure.

FIG. 6 illustrates the application of the clip of the present invention to body tissue. As can be seen in FIG. 6, a tubular organic structure such as blood vessel 300 is clipped in two locations with clips 100 of the present invention, thereby closing interior passageway 320 of the blood vessel and permitting a division 310 of the blood vessel by a knife blade slicing between the clips 100. Clips 100 seal the newly created ends of the blood vessel 300 such that the flow of blood therethrough is completely occluded. However, while the flow of blood through the vessel passageway 320 is stopped, openings 143 created by the intersection of the indentations 140 with one of the side surfaces 111a permit the flow of nourishing body fluid within the wall of blood vessel 300 to the portion of the blood vessel tissue located in the indentations 140. This advantageous feature reduces the possibility of tissue necrosis.

While FIG. 6 illustrates a ligating and dividing operation accomplished by instruments well known in the art, other operations where surgical clips are called for are contemplated as suitable applications for the clips of the present invention. Thus, a clip may be used singly, or in combination with other clips, the clips may be applied to various types of organic body structures which may or may not be divided, depending on the type of operation being performed.

EXAMPLE 1

Samples were provided of titanium clips of the present invention as illustrated in FIGS. 1 to 5 and the foregoing description.

Figure 7:
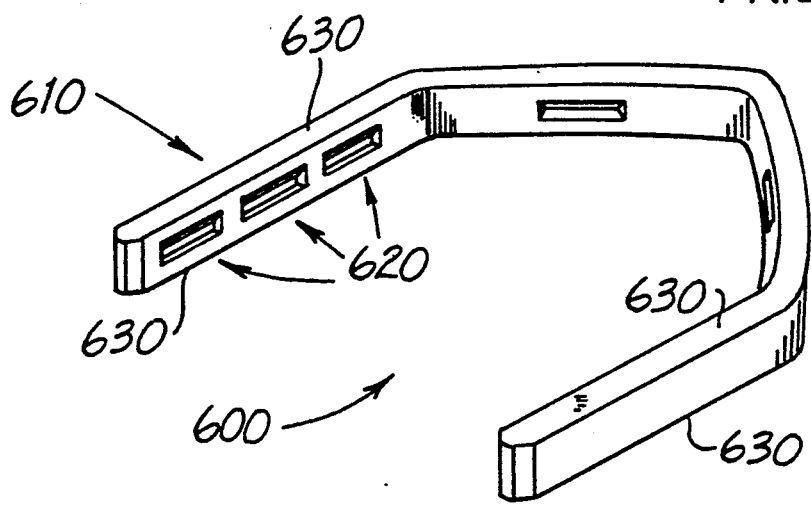
FIG. 7 is a perspective view of a prior art clip.

For comparison, samples were provided of titanium clips of known configuration as illustrated in FIG. 7, i.e., a prior art design not contemplated as an embodiment of the present invention.

Both types of clips were of the same size and shape except for the configuration of the indentations. The prior art samples 600 included on each leg 610 a set of generally V-shaped notches 620 which did not intersect with the side surfaces 630.

A surgical clip applying instrument was provided and alternately loaded and fired with clips of the present invention and the prior known clip described above.

Clips were applied to blood vessels of various sizes, and to porcine cystic duct tissue to determine which type clip provided higher (i.e. better) pull force, i.e., the force necessary to pull the clip off the vessel. The following results were obtained:

1. Blood vessel test—There was no observed statistical difference between the mean pull force of each clip. However, the prior art clip exhibited lower individual pull force data points, i.e., 100 gram pull force for the clip of the present invention versus 60 gram pull force for the prior art clip.

2. Porcine cystic duct—The clips of the present invention exhibited a higher mean pull force, 77.5 grams, versus a 52.5 gram means pull force for the prior art clip. The clips of the present invention also had higher individual low data points, i.e., 70 grams pull force, versus the 40 gram pull force of the prior art clip.

These data show that the clips of the present invention provide improved resistance to being dislodged from body tissue as compared with the prior known clip.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A hemostatic clip for application to body tissue, which comprises:
   first and second legs, each leg having a tissue contacting surface and at least two side surfaces intersecting said tissue contacting surface and defining a width of said leg therebetween, said tissue contacting surface having at least one indentation disposed thereon across less than the entire width of the tissue contacting surface and intersecting one of said side surfaces, said indentation being completely defined by at least one wall which intersects said tissue contacting surface and an indentation base surface which intersects said wall and said one side surface.

2. The hemostatic clip of claim 1, wherein the intersection of said indentation with said side surface defines an open area in said side surface to permit the flow of body fluid therethrough to body tissue.

3. The hemostatic clip of claim 1, wherein said clip comprises a plurality of said indentations arranged in first and second rows, said indentations intersecting with a respective one or the other of said side surfaces.

4. The hemostatic clip of claim 3, wherein the indentations of one of said first and second rows are in staggered arrangement with respect to the indentations of the other of said first and second rows.

5. The hemostatic clip of claim 3, wherein said first and second legs each include a distal end portion, said distal end portions of said first and second legs extending in generally parallel orientation to each other, and said legs each further including a proximal portion, said proximal portions being joined at an angle so as to define an apex and a bail portion of the hemostatic clip.

6. The hemostatic clip of claim 5, wherein said bail portion is generally V-shaped.

7. The hemostatic clip of claim 6, wherein the angle between the proximal portions of the first and second legs is from about 129° to about 131°.

8. The hemostatic clip of claim 5, wherein said bail portion is generally U-shaped.

9. The hemostatic clip of claim 5, further including at least one notch extending lengthwise on at least one of said proximal portions.

10. The hemostatic clip of claim 9, wherein said notch has a V-shaped cross section.

11. The hemostatic clip of claim 5, wherein the indentations are located on the tissue contacting surfaces of the distal end portions of the first and second legs.

12. The hemostatic clip of claim 1, wherein said wall includes at least one edge formed by the intersection of said wall with a respective one of said side surfaces.

13. The hemostatic clip of claim 12, wherein said wall is of generally arcuate configuration.

14. The hemostatic clip of claim 12, wherein said wall is of generally semicircular configuration.

15. The hemostatic clip of claim 12, wherein said wall is substantially perpendicular to the tissue contacting surface.

16. The hemostatic clip of claim 1, wherein said clip is fabricated from a material selected from the group consisting of stainless steel, tantalum, titanium, and plastic.

17. A hemostatic clip for application to body tissue, which comprises:
first and second legs, each leg having a tissue contacting surface and at least two side surfaces intersecting said tissue contacting surface and defining a width of said leg therebetween, said first and second legs being formable from a relatively spaced apart position for reception of tissue therebetween to a closed position wherein the legs are in close proximity to each other for clamping tissue therebetween, said tissue contacting surface having at least one indentation disposed thereon across less than the entire width of the tissue contacting surface and intersecting one of said side surfaces, said indentation being completely defined by at least one wall which intersects said tissue contacting surface and an indentation base surface which intersects said wall and said one side surface.

18. A hemostatic clip for application to body tissue, which comprises:
first and second legs, each leg having a substantially flat tissue contacting surface and at least two side surfaces intersecting said tissue contacting surface and defining a width of said leg therebetween, said tissue contacting surface having at least one indentation disposed thereon across less than the entire width of the tissue contacting surface and intersecting one of said surfaces, said indentation being completely defined by a wall which intersects said tissue contacting surface and an indentation base surface which intersects said wall and one of said side surfaces, the depth of said at least one indentation being less than the depth of the leg on which the indentation is disposed.

19. A hemostatic clip for application to body tissue, which comprises:
first and second legs, each leg having a substantially flat tissue contacting surface and at least two side surfaces intersecting said tissue contacting surface and defining a width of said leg therebetween, said flat tissue contacting surface having at least one indentation disposed thereon across less than the entire width of the tissue contacting surface and intersecting one of said side surfaces, said indentation having at least one wall oriented transverse to said flat tissue contacting surface and a base surface which intersects said wall and said one side surface, said wall and said base surface completely defining said indentation.

* * * * *